(12) United States Patent
Amazeen et al.

(10) Patent No.: US 7,821,643 B2
(45) Date of Patent: Oct. 26, 2010

(54) COMMON PATH SYSTEMS AND METHODS FOR FREQUENCY DOMAIN AND TIME DOMAIN OPTICAL COHERENCE TOMOGRAPHY USING NON-SPECULAR REFERENCE REFLECTION AND A DELIVERING DEVICE FOR OPTICAL RADIATION WITH A PARTIALLY OPTICALLY TRANSPARENT NON-SPECULAR REFERENCE REFLECTOR

(75) Inventors: Paul G. Amazeen, Cleveland, OH (US); Felix I. Feldchtein, Framingham, MA (US)

(73) Assignee: Imalux Corporation, Cleveland, OH (US)

( * ) Notice: Subject to any disclaimer, the term of this patent is extended or adjusted under 35 U.S.C. 154(b) by 402 days.

(21) Appl. No.: 11/850,399

(22) Filed: Sep. 5, 2007

(65) Prior Publication Data

US 2008/0055603 A1 Mar. 6, 2008

Related U.S. Application Data

(60) Provisional application No. 60/824,713, filed on Sep. 6, 2006.

(51) Int. Cl.
*G01B 9/02* (2006.01)
(52) U.S. Cl. .................................... 356/479
(58) Field of Classification Search ........... 356/479, 356/497
See application file for complete search history.

(56) References Cited

U.S. PATENT DOCUMENTS

| | | | |
|---|---|---|---|
| 6,882,433 B2 * | 4/2005 | Marron et al. ............. 356/512 |
| 7,057,742 B2 | 6/2006 | Marron et al. | |
| 2004/0239938 A1 | 12/2004 | Izatt | |
| 2004/0239942 A1 | 12/2004 | Sun | |
| 2005/0041258 A1 | 2/2005 | Opsal et al. | |
| 2006/0091334 A1 | 5/2006 | Urbach et al. | |
| 2006/0109478 A1 | 5/2006 | Tearney et al. | |
| 2006/0132791 A1 | 6/2006 | Toida et al. | |
| 2007/0008545 A1 * | 1/2007 | Feldchtein et al. ......... 356/479 |

OTHER PUBLICATIONS

International Search Report and Written Opinion for International Application No. PCT/US07/77706 dated Mar. 24, 2008.

* cited by examiner

*Primary Examiner*—Tarifur Chowdhury
*Assistant Examiner*—Jonathon D Cook
(74) *Attorney, Agent, or Firm*—Renner, Otto, Boisselle & Sklar, LLP

(57) ABSTRACT

Provided are common path frequency domain and time domain OCT systems and methods that use non-specular reference reflection for obtaining internal depth profiles and depth resolved images of samples. Further provided is a delivering device for optical radiation, preferably implemented as an optical fiber probe with a partially optically transparent non-specular reflector placed in the vicinity of an associated sample. High frequency fringes are substantially reduced and a stable power level of the reference reflection is provided over the lateral scanning range. The partially optically transparent non-specular reflector is implemented as a coating placed on the interior surface of the optical probe window including spots of a metal, or a dielectric coating, separated by elements of another coating or just spaces of a clean substrate. In an alternative embodiment, the scattering elements are made 3-dimensional, having, for example, a spherical shape.

7 Claims, 6 Drawing Sheets

COMMON PATH SYSTEMS AND METHODS FOR FREQUENCY DOMAIN AND TIME DOMAIN OPTICAL COHERENCE TOMOGRAPHY USING NON-SPECULAR REFERENCE REFLECTION AND A DELIVERING DEVICE FOR OPTICAL RADIATION WITH A PARTIALLY OPTICALLY TRANSPARENT NON-SPECULAR REFERENCE REFLECTOR

CROSS-REFERENCE TO RELATED APPLICATIONS

This application is based on and claims priority to U.S. Provisional Patent Application Ser. No. 60/824,713, filed on Sep. 6, 2006, the entirety of which is incorporated herein.

BACKGROUND OF THE INVENTION

The subject application relates generally to systems and methods for visualizing subsurface regions of samples. In particular, the subject application is directed to common path systems and methods for frequency domain and time domain optical coherence tomography using non-specular reference reflection for providing internal depth profiles and depth resolved images of samples. The subject application is also directed to a delivering device for optical radiation, preferably implemented as an optical fiber probe with a partially optically transparent non-specular reflector to be used in common path frequency domain and time domain optical coherence tomography and reflectometry devices.

As known in the art, optical coherence reflectometry/tomography (OCT) involves splitting an optical radiation into at least two portions, and directing one portion of the optical radiation toward a subject of investigation. The subject of investigation will be further referred to as a "sample", whereas the portion of optical radiation directed toward an associated sample will be further referred to as a "sample portion" of optical radiation. The sample portion of optical radiation is directed toward an associated sample by means of a delivering device, such as, for example, an optical probe. Another portion of the optical radiation, which will be further referred to as "reference portion", is used to produce a combination optical radiation representative of an optical radiation reflected or backscattered from an associated sample.

In a typical common path OCT device, the sample and reference portions of the optical radiation propagate via the same optical path and reference reflection is created in the distal part of the OCT delivering device, which is typically implemented as an optical fiber probe. Common path OCT is insensitive to the length of the optical probe, material dispersion, and polarization changes associated with bending of the optical fiber, which makes it very easy to manufacture and user friendly. Typically, an optical power of several microwatts represents the optimal level for the power of the reference portion in common path OCT. It is also strongly preferred that the power level of the reference portion does not change as lateral (reciprocal or rotational) scanning occurs in the optical probe. Known solutions of obtaining a stable reference reflection with appropriate power level include reflection from an angle cleaved fiber tip, or specular reflection from an internal surface of the probe output window, combined with telecentric optics. Unfortunately, a telecentric optical system for the OCT optical probe requires substantially more space than a regular optical system, which makes it impractical for implementation in optical probes of critical dimensions, such as miniature endoscopic optical probes. In addition, the telecentric optical system is more expensive and difficult to assemble and align.

As to the operation of common path OCT systems, using a reflection from a tip of the optical fiber as the reference portion, is known to work perfectly for time domain OCT, however it leads to serious problems for frequency domain OCT. Even in a miniaturized probe, the optical path from the fiber tip to the sample surface and back is much larger than the intended "scanning depth". Therefore, direct spectral analysis of the optical radiation mix coming back from the optical probe and consisting of sample and reference portions of the optical radiation, axially separated by 20 mm or more, results in very high frequency fringes and requires excessive spectral resolution of the frequency domain OCT system and is an extreme burden for the data acquisition and signal processing system. An alternative solution is to use a secondary interferometer to reduce the optical path length shift between the sample and reference portions of optical radiation to approximately 1 mm or less.

However, this solution for common path frequency domain OCT is prone to an additional noise originating from interference between two replicas of the reference radiation, which can make questionable a practical realization of the secondary interferometer layout. In time domain common path OCT systems, a secondary interferometer is necessarily required, because the optical path difference between reference and sample potions of the optical radiation has to be scanned to obtain an in-depth profile. Fortunately, the additional noise problems are not inherent to time domain common path OCT systems. However, using an angle cleaved tip of the optical fiber with high reproducibility of the cleave angle and reflection level, is technologically challenging.

Yet another solution is to build an optical system with stable specular reflection from the internal surface of the optical probe output window using non-telecentric optics. Unfortunately, in a typical OCT probe optical system using non-telecentric optics, the beam incidence angle to the probe output window changes in the course of lateral scanning. Thus, the requirements for good coupling of the optical radiation back to the optical fiber and maintaining the necessary coupling over the lateral scanning range are contradictory to each other. Therefore, it could be very problematic or impossible to get a stable level of the reference reflection from a specular reflector located in the distal part of the optical fiber probe.

SUMMARY OF THE INVENTION

In accordance with the subject application, there are provided common path systems and methods for frequency domain and time domain optical coherence reflectometry/tomography that overcome the above mentioned problems and provide a stable power level of the non-specular reference reflection, which is used for producing a combination optical radiation representative of the optical radiation, reflected or backscattered from an associated sample.

Further, in accordance with the subject application, there are provided common path systems and methods for frequency domain and time domain optical coherence reflectometry/tomography that maintain a predetermined and stable power level of the non-specular reference reflection over a lateral scanning range.

Still further, in accordance with the subject application, there is provided a delivering device for use in common path time domain and frequency domain optical coherence tomography and reflectometry for delivering optical radiation to an associated sample maintaining a predetermined and stable power level of a non-specular reference reflection using simple non-telecentric optics.

Yet further, in accordance with the subject application, there is provided an optical fiber probe for use in common path time domain and frequency domain optical coherence tomography and reflectometry that provides a stable power level of a non-specular reference reflection over a lateral scanning range.

Still further in accordance with the subject application, there is provided a miniature optical fiber probe for use in common path time domain and frequency domain optical coherence tomography and reflectometry devices intended for biomedical applications that provides stable reference reflection using simple non-telecentric optics and a partially optically transparent non-specular reference reflector.

Further, in accordance with one embodiment of the subject application, there is provided a common path frequency domain optical coherence reflectometry device. The device comprises means adapted for generating an optical radiation, delivering means, and directional means, optically coupled with the means adapted for generating optical radiation and adapted for directing the optical radiation from the means adapted for generating optical radiation to the proximal part of the delivering means. The delivering means comprise a proximal part and a distal part. The distal part of the delivering means includes a focusing system and a partially optically transparent non-specular reference reflector, which is optically coupled with the focusing system. The delivering means is adapted for forming and delivering an optical radiation beam to the partially optically transparent non-specular reference reflector, and delivering a first portion of the optical radiation beam to an associated sample via the partially optically transparent non-specular reference reflector placed in a vicinity of an associated sample, along a common optical path. The common path frequency domain optical coherence reflectometry device further comprises frequency domain optoelectronic registering means optically coupled with the directional means and comprising data processing and displaying means. The partially optically transparent non-specular reference reflector is adapted for splitting the optical radiation beam into two portions prior to delivery of the first portion of the optical radiation beam to an associated sample, wherein the second portion is reflected by the partially optically transparent non-specular reference reflector. The partially optically transparent non-specular reference reflector is further adapted for creating a combination optical radiation by combining an optical radiation returning from an associated sample with a non-specular reference optical radiation reflected from the partially optically transparent non-specular reference reflector. The delivering means is further adapted for delivering the combination optical radiation to the directional means, wherein the directional means is further adapted for directing the combination optical radiation to the frequency domain optoelectronic registering means.

Further, in accordance with one embodiment of the subject application, there is provided a method for common path frequency domain optical measurements in accordance with the device as set forth above.

Still further, in accordance with one embodiment of the subject application, there is provided a common path time domain optical coherence reflectometry device. The device is specified by a longitudinal range of interest having at least a front boundary, and at least partially overlapping with an associated sample. The device comprises means adapted for generating an optical radiation and optical means optically coupled with the means adapted for generating an optical radiation. The optical means is adapted for splitting the optical radiation into a first and second replicas of the optical radiation, propagating with an optical path length difference. The device further comprises delivering means comprising a proximal part and a distal part including a focusing system and a partially optically transparent non-specular reference reflector, which is optically coupled with the focusing system. The delivering means is adapted for forming and delivering an optical radiation beam to the partially optically transparent non-specular reference reflector, and delivering a first portion of the optical radiation beam to an associated sample via the partially optically transparent non-specular reference reflector placed in a vicinity of an associated sample at a predetermined optical path length from the front boundary of the longitudinal range of interest of an associated sample, along a common optical path. The common path time domain optical coherence reflectometry device also comprises directional means optically coupled with the optical means and optically coupled with the delivering means, and adapted for directing the two replicas of optical radiation form the optical means to the proximal part of the delivering means. Further included in the device is time domain optoelectronic registering means optically coupled with the directional means and comprising data processing and displaying means. The optical means includes means adapted for changing the optical path length difference between the first and second replicas of the optical radiation. The optical path length difference between the first and second replicas of optical radiation is generally equal to the predetermined optical path length between the partially optically transparent non-specular reference reflector and the front boundary of the longitudinal range of interest. The partially optically transparent non-specular reference reflector is adapted for splitting the optical radiation beam including the first and second replicas, into two portions prior to delivery of the first portion of the optical radiation beam, including the first and second replicas, to an associated sample. The second portion of the optical radiation beam including the first and second replicas, is reflected by the partially optically transparent non-specular reference reflector. The partially optically transparent non-specular reference reflector is further adapted for combining an optical radiation representative of one replica, returning from an associated sample, with a non-specular reference optical radiation, representative of the other replica, reflected from the partially optically transparent non-specular reference reflector. The delivering means is further adapted for delivering the combination optical radiation to the directional means, and the directional means is further adapted for directing the combination optical radiation to the time domain optoelectronic registering means.

Further, in accordance with one embodiment of the subject application, there is provided a method for common path time domain optical measurements in accordance with the device as set forth above.

Yet further, in accordance with one embodiment of the subject application, there is provided a common path time domain optical coherence reflectometry device. The device is specified by a longitudinal range of interest having at least a front boundary, and at least partially overlapping with an associated sample. The device comprises means adapted for generating an optical radiation and delivering means comprising a proximal part and a distal part. The distal part of the delivering means includes a focusing system and a partially optically transparent non-specular reference reflector, which is optically coupled with the focusing system. The delivering means is adapted for forming and delivering an optical radiation beam to the partially optically transparent non-specular reference reflector, and delivering a first portion of the optical radiation beam to an associated sample via the partially optically transparent non-specular reference reflector placed in a vicinity of an associated sample at a predetermined optical path length from the front boundary of the longitudinal range of interest of an associated sample, along a common optical path. Further comprised in the common path time domain optical coherence reflectometry device, is directional means optically coupled with the means adapted for generating an optical radiation. The directional means is adapted for directing the optical radiation from the means adapted for producing an optical radiation to the proximal part of the delivering means. Also included in the device is optical means optically coupled with the directional means, and time domain optoelectronic registering means optically coupled with the optical means and comprising data processing and displaying means. The partially optically transparent non-specular reference reflector is adapted for splitting the optical radiation beam into two portions prior to delivery of the first portion of the optical radiation beam to an associated sample. The second portion is reflected by the partially optically transparent non-specular reference reflector. The delivering means is further adapted for delivering an optical radiation returning from an associated sample and an optical radiation reflected from the partially optically transparent non-specular reference reflector to the directional means. The directional means is further adapted for directing the optical radiation returning from an associated sample and the optical radiation reflected from the non-specular reference reflector to the optical means. The optical means is adapted for splitting the optical radiation returning from an associated sample into a first and second replicas propagating therethrough with an optical path length difference, which is generally equal to the predetermined optical path length between the non-specular reference reflector and the front boundary of the longitudinal range of interest. The optical means is further adapted for splitting the optical radiation reflected from the partially optically transparent non-specular reference reflector into a first and second non-specular reference replicas propagating therethrough with an optical path length difference, which is generally equal to the optical path length difference for the first and second replicas of the optical radiation returning from an associated sample. The optical means comprises means adapted for changing the optical path length difference for the respective first and second replicas and is further adapted for creating a combination optical radiation by combining a replica of the optical radiation returning from an associated sample with a respective non-specular reference replica of the non-specular optical radiation reflected from the partially optically transparent non-specular reference reflector.

Further, in accordance with one embodiment of the subject application, there is provided a method for common path time domain optical measurements in accordance with the device as set forth above.

Still further, in accordance with one embodiment of the subject application, there is provided a delivering device for optical radiation. The delivering device comprises an optical system adapted for receiving incident optical radiation. The optical system includes a focusing system and a partially optically transparent non-specular reference reflector optically coupled with the focusing system and placed in a vicinity of an associated sample. The optical system is further adapted for forming and delivering an optical radiation beam to the partially optically transparent non-specular reference reflector, and delivering a first portion of the optical radiation beam to an associated sample via the partially optically transparent non-specular reference reflector placed in a vicinity of an associated sample, along a common optical path. The partially optically transparent non-specular reference reflector is adapted for splitting the optical radiation beam into two portions prior to delivery of the first portion of the optical radiation beam to an associated sample. Further, the partially optically transparent non-specular reference reflector is adapted for reflecting the second portion of the optical radiation beam.

Still other aspects of the subject application will become readily apparent to those skilled in this art from the following description wherein there are shown and described preferred embodiments of the subject application, simply by way of illustration of the best modes suited to carry out the subject application. As it will be realized, the subject application is capable of other different embodiments and its several details are capable of modifications in various obvious aspects all without departing from the scope of the subject application. Accordingly, the drawings and description will be regarded as illustrative in nature and not as restrictive.

BRIEF DESCRIPTION OF THE DRAWINGS

The accompanying drawings incorporated in and forming a part of the specification, illustrate several aspects of the subject application and together with the description serve to explain the principles of the subject application.

DETAILED DESCRIPTION OF THE INVENTION

The subject application is directed to systems and methods for visualizing subsurface regions of samples, and more specifically, to common path systems and methods for frequency domain and time domain optical coherence tomography (OCT) using a partially optically transparent non-specular reference reflector for providing internal depth profiles and depth resolved images of samples. The subject application is also directed and to a device for delivering optical radiation to an associated sample, preferably implemented as an optical fiber probe with a partially optically transparent non-specular reflector. The delivering device of the subject application is capable of being efficiently used in common path frequency domain and time domain reflectometry, as well. The common path frequency domain and time domain OCT devices are illustrated herein by means of examples of optical fiber devices, although it is evident that they may be implemented with the use of bulk optic elements. The delivering device is illustrated as an optical fiber implementation, which is preferable for use in medical applications, especially in endoscopy, where flexibility of the optical fiber provides convenient access to different tissues and organs, including internal organs via an endoscope. However, the whole device, or any part of it, is capable of implementation using traditional bulk optics: mirrors, prisms, and the like, and the delivering device may be used as an independent device.

Figure 1:
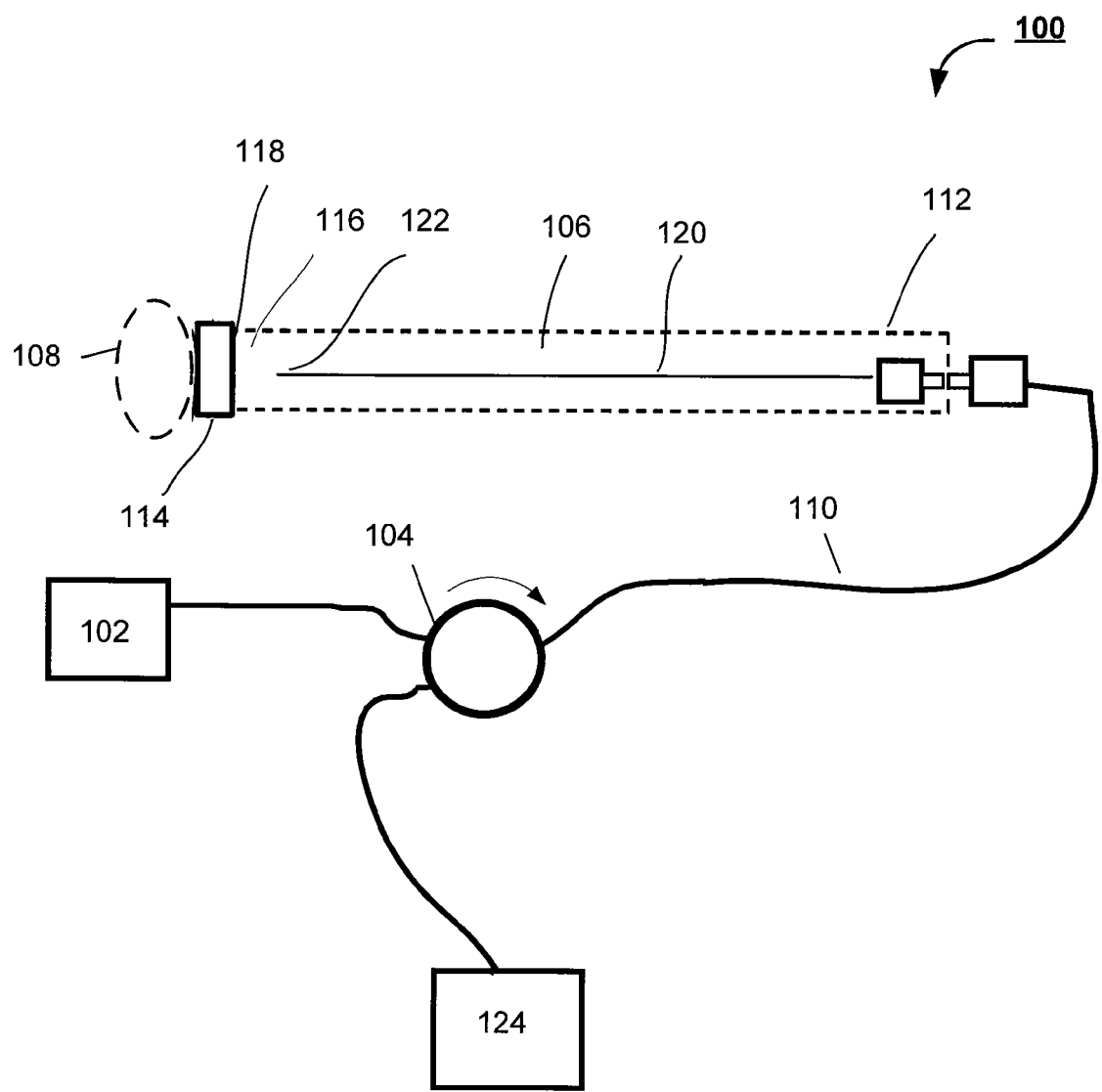
FIG. 1 is a schematic diagram of a common path frequency domain optical coherence tomography device according to one embodiment of the subject application.

Referring now to FIG. 1, there is shown a schematic block diagram of a common path frequency domain reflectometry/tomography device 100 in accordance with one embodiment of the subject application. As shown in FIG. 1, the common path frequency domain OCT device 100 includes a source 102 of optical radiation optically coupled with directional means 104. In a preferred embodiment, the source 102 operates in the visible or near IR range. A skilled artisan will appreciate that the source 102 is capable of being implemented as, for example, and without limitation, a semiconductor superluminescent diode, doped-fiber amplified spontaneous emission superlum, solid state and fiberoptic femtosecond laser. The common path frequency domain reflectometry/tomography device 100 also includes a delivering device, which in the embodiment of FIG. 1 is implemented as an optical fiber probe 106. The optical fiber probe 106 is optically coupled with the directional means 104. A skilled artisan will appreciate that the directional means 104 is capable of implementation, for example, and without limitation, as a circulator or a directional coupler, as known in the art. The optical fiber probe 106, as will be recognized by those skilled in the art, includes a focusing system that is capable of being implemented, as known in the art, as a lens or lens system (not shown) in its distal part 116. In the embodiment of FIG. 1, the optical fiber probe 106 is optically coupled with the directional means 104 via an optical fiber 110.

In the embodiment depicted in FIG. 1, the optical fiber probe 106 includes a proximal part 112, an output window 114, and a distal part 116. The output window 114 is placed in a vicinity of an associated sample 108. The distal part 116 of the optical fiber probe 106 further includes a partially optically transparent non-specular reference reflector 118, which in the embodiment of FIG. 1 is attached to an interior surface of the output window 114. Those skilled in the art will recognize that non-specular reflectance is a reflectance other than a mirror reflectance that occurs at an angle equal and opposite to an incident angle, such as diffuse reflectance. The optical fiber probe 106 provides forming and delivering of an optical radiation beam to the partially optically transparent non-specular reference reflector 118, and delivering a first portion of the optical radiation beam to an associated sample 108 (sample portion) via the partially optically transparent non-specular reference reflector 118, along a common optical path.

In this embodiment, the partially optically transparent non-specular reference reflector 118 also provides splitting of the optical radiation delivered from the source 102 into two portions, prior to delivery of the first portion of the optical radiation beam to an associated sample 108. The second portion is reflected by the partially optically transparent non-specular reference reflector 118 and serves as a non-specular reference reflection (reference portion). The optical fiber probe 106 further includes an optical fiber 120 with a tip 122. The tip 122 of optical fiber 120 is capable of being moved in a plane generally perpendicular to the axis of the optical fiber 120 for providing lateral scanning, as known in the art. The optical fiber probe 106 will be described in greater detail below with reference to FIG. 2. The common path frequency domain OCT device 100 further includes a frequency domain optoelectronic registering unit 124 optically coupled with the directional means 104. The frequency domain optoelectronic registering unit 124 includes a data processing and displaying unit (not shown in the drawing). A skilled artisan will appreciate that the frequency domain optoelectronic registering unit 124 is capable of implementation as any suitable registering unit known in the art.

In one embodiment of the subject application, the source 102 of optical radiation is narrowband and tunable, whereas the frequency domain optoelectronic registering unit 124 includes at least one photodetector connected with the data processing and displaying unit (not shown in FIG. 1). In another embodiment the source 102 is broadband and implemented as a source of low-coherence optical radiation. In this embodiment a spectrometer instead of a single photodiode is used in the frequency domain optoelectronic registering unit 124, therefore parallel registration is performed instead of sequential.

Figure 2:
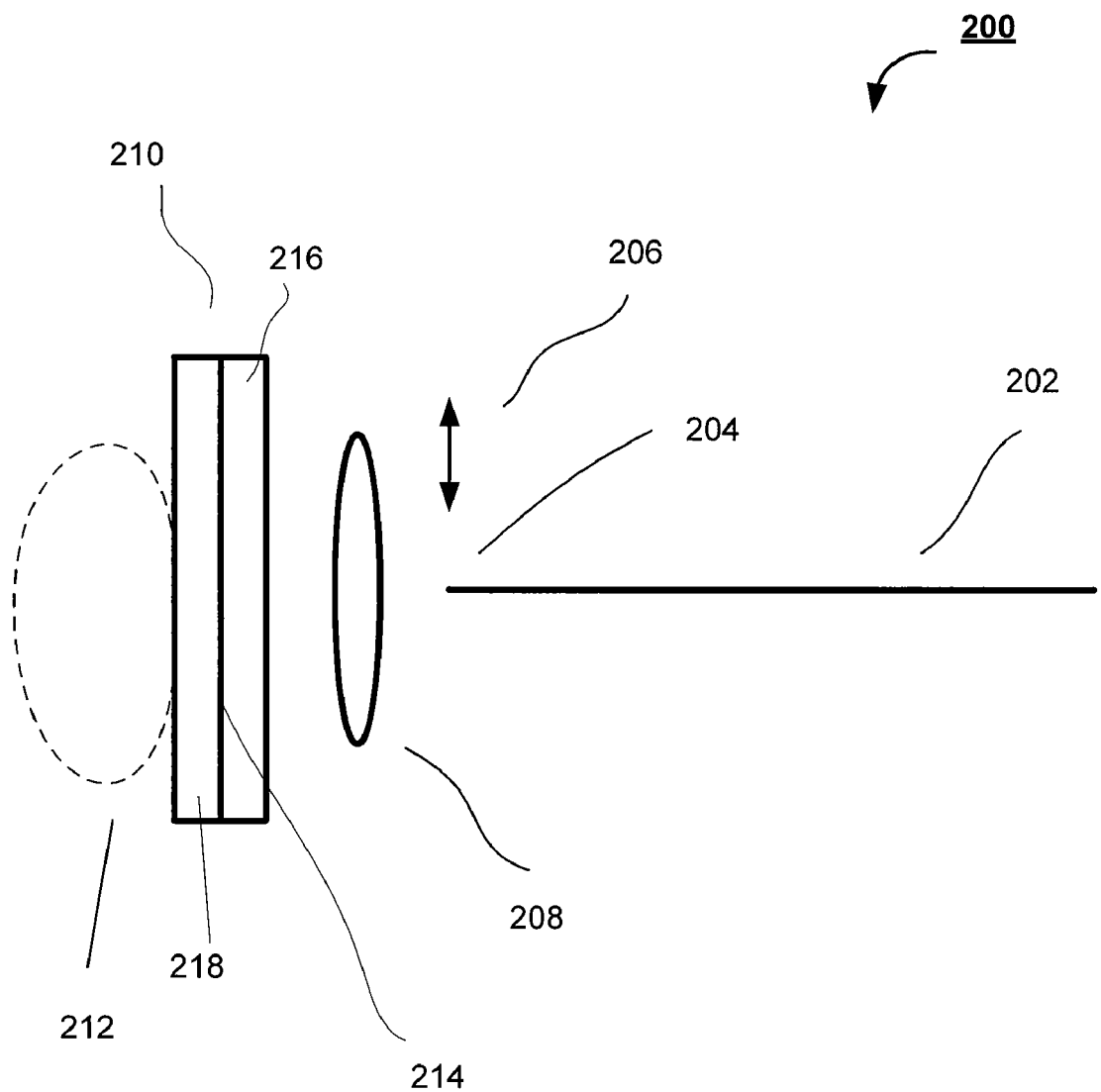
FIG. 2 is a schematic diagram illustrating an optical fiber probe with a partially optically transparent non-specular reference reflector according to one embodiment of the subject application.

Turning now to FIG. 2, there is shown a schematic diagram of an optical fiber probe 200 with a partially optically transparent non-specular reference reflector in accordance with one embodiment of the subject application. The optical fiber probe 200, as described herein, is designed specifically for use in a common path optical coherence reflectometry/tomography device in accordance with the subject application, such as illustrated, for example, in FIG. 1, FIG. 3, and FIG. 4, and designated as the optical fiber probe 106, 328, and delivering means 410, respectively. However, as will be understood by a skilled artisan, the optical fiber probe 200 is capable of being used as an independent device in a suitable application.

As shown in FIG. 2, the optical fiber probe 200 includes an optical fiber 202. In a preferred embodiment, the tip 204 of optical fiber 202 is capable of being moved in a plane generally perpendicular to the axis of the optical fiber 202 for providing lateral scanning, such as reciprocal scanning or rotational scanning. As will be appreciated by those skilled in the art, lateral scanning is capable of being implemented using any suitable means known in the art. Arrows 206 indicate a possible movement of the tip 204 of the optical fiber 202. The optical fiber probe 200 also includes a focusing system indicated in FIG. 2 as a lens 208. The optical fiber probe 200 further includes an output window 210 placed in the vicinity of an associated sample 212. The optical fiber probe 200 further includes a partially optically transparent non-specular reference reflector 214, which in the embodiment of FIG. 2 is an integral part of the output window 210. The output window 210 includes a proximal part 216 and a distal part 218. As depicted in FIG. 2, the proximal part 216 of the output window 210 is optically coupled with the distal part 218 of the output window 210 via the partially optically transparent non-specular reference reflector 214.

As will be appreciated by those skilled in the art, the partially optically transparent non-specular reference reflector 214 is capable of being implemented as a non-specular coating. With respect to the embodiment, illustrated in FIG. 2, the proximal part 216 of the output window 210 is capable of having the non-specular coating on its exterior surface. In this embodiment, the partially optically transparent non-specular reference reflector 214 is an integral part of the proximal part 216, and the non-specular coating is suitably adhesively attached to an interior surface of the distal part 218 the output window 210. Alternatively, the distal part 218 the output window 210 is capable of having the non-specular coating on its interior surface. In this embodiment, the partially optically transparent non-specular reference reflector 214 is an integral part of the distal part 218 and the non-specular coating is suitably adhesively attached to an exterior surface of the proximal part 218 the output window 210. A skilled artisan will understand that in any case, a refraction index matching adhesive is desirable in the gap between these referred surfaces of the output window 210 to minimize specular reflection. As will be further appreciated by those skilled in the art, the optical beam may have normal incidence to these surfaces at some point of the lateral scanning, for example, in the center. However, with sufficient quality of index matching, specular reflections comparable with the non-specular reflection level will still be avoided. In another embodiment, to avoid the necessity of high accuracy of index matching the partially optically transparent non-specular reference reflector 214 may be tilted with respect to the surface of lateral scanning, the latter minimizing the specular reflection from it.

The partially optically transparent non-specular reference reflector 214 is specified by a predetermined backscattering indicatrix that is, preferably, at least several times broader than a predetermined angle of view of the optical system for the optical radiation coupling back to the optical fiber, taking into account the range of lateral scanning of an associated sample. As will be recognized by those skilled in the art, the latter (expressed in radians) is defined substantially by a ratio of the optical fiber numerical aperture and the optical system magnification. When this condition (appropriate angular width of the backscattering indicatrix) is met, the optical radiation is quite efficiently coupled back to the optical fiber 202 and yet the changes in the power level of the reference reflection, associated with the lateral scanning, are minimized. As will be appreciated by those skilled in the art, the output window 210 is at least partially optically transparent to allow for delivering of the optical radiation beam to an associated sample 212.

Preferably, the partially optically transparent non-specular reference reflector 214 in accordance with the subject application, includes inhomogeneities with feature sizes substantially smaller than the OCT beam size at the reference position. The later is illustrated by the following numerical example. A forward looking optical fiber probe with a zero working distance, such as illustrated in FIG. 2 (intended to work in contact with an associated sample 212), typically has a beam waist located at ~0.5 mm from the exterior surface of the output window 210. The output window 210 is typically made as thin as practical, yet maintaining mechanical integrity, which is in the 0.3-0.5 mm range. The optimal beam waist diameter for OCT is typically 15-25 μm, because optical radiation diffraction prevents tighter focusing over the entire axial range of interest (1-2 mm). Given the above conditions, the converging beam diameter at the partially optically transparent non-specular reference reflector 214 is expected to be 30-40 μm. Therefore the partially optically transparent non-specular reference reflector 214 preferably, comprises scattering/reflecting elements with a size of the order of 1 μm or less and separated by a distance of several μm or less. Thus, as will be recognized by a skilled artisan, in the process of lateral scanning the optical radiation beam will at all times hit a sufficient number of scattering/reflecting elements, providing an averaged reflection coefficient that substantially does not fluctuate during lateral scanning.

In another preferred embodiment, the reflecting/scattering elements of the partially optically transparent non-specular reference reflector are implemented as spots of a metal or a dielectric coating, separated by elements of another coating or just spaces of a clean substrate. As will be appreciated by a skilled artisan, the coating is preferably implemented as a thin film coating, as known in the art. In an alternative embodiment, the scattering elements are made 3-dimensional, having, for example and without limitation, a spherical shape, which is known to have retroreflective properties. As will be appreciated by those skilled in the art, different shapes and spacing configuration for the scattering elements are capable of being considered, depending on the desired scattering indicatrix properties and technological availability. In particular, element spacing is capable of being regular (periodic) with different types of translational and angular symmetry (square, rhomboid, hexagonal etc). Those skilled in the art will recognize that the scattering elements preferably cover approximately 2% to 10% of the substrate surface, leaving approximately 90% to 98% for ballistic transmission of the optical radiation.

Figure 3:
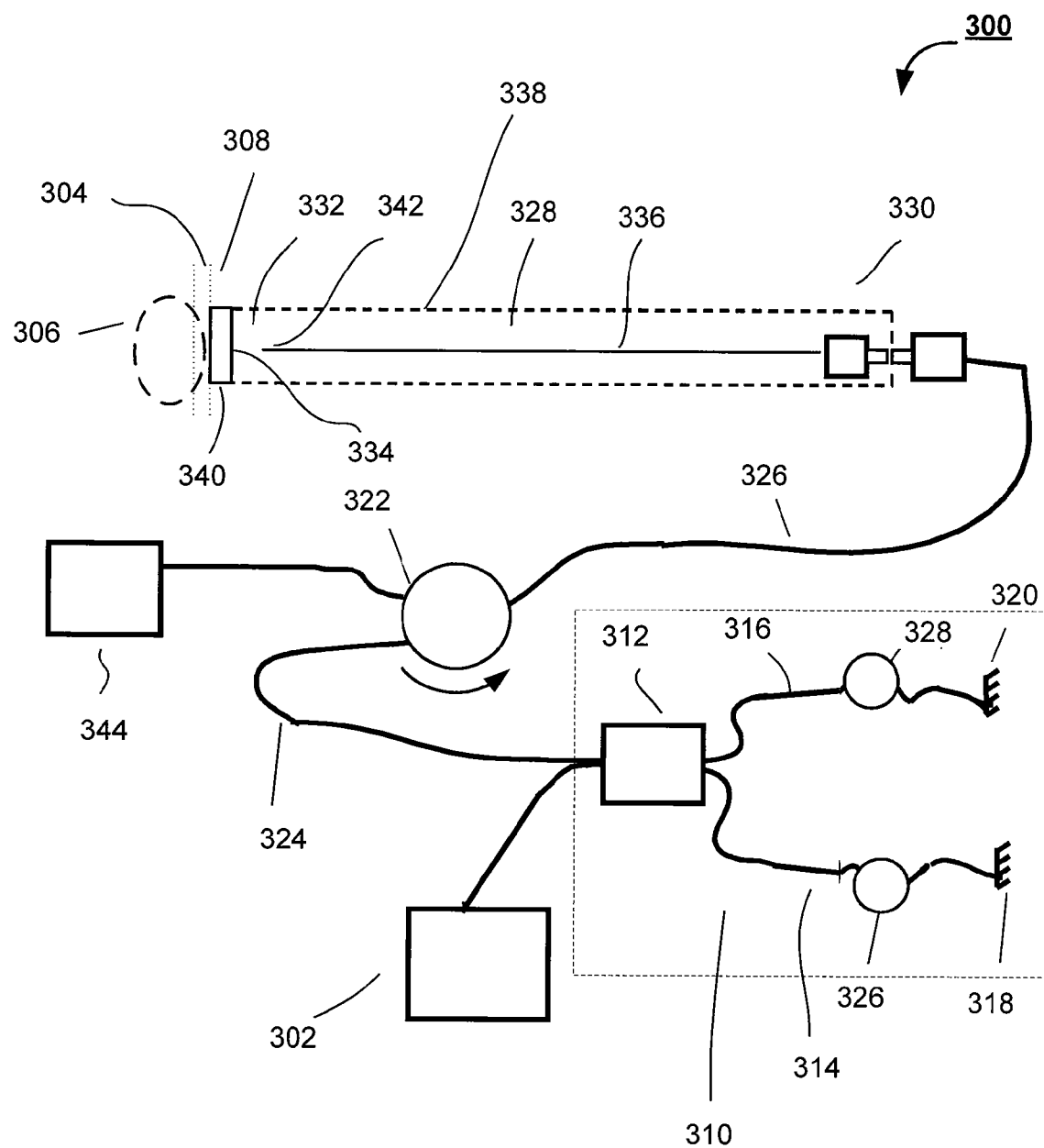
FIG. 3 is a schematic diagram of a common path time domain optical coherence tomography device according to one embodiment of the subject application.

Turning now to FIG. 3, there is shown a block diagram of a common path time domain reflectometry/tomography device 300 in accordance with one embodiment of the subject application. As shown in FIG. 3, the common path time domain OCT device 300 includes a source 302 of optical radiation optically coupled with optical means. In a preferred embodiment, the source 302 operates in the visible or near IR range. A skilled artisan will appreciate that the source 302 is capable of being implemented as, for example, and without limitation, a semiconductor superluminescent diode, doped-fiber amplified spontaneous emission superlum, solid state and fiberoptic femtosecond laser. The common path time domain optical coherence tomography device 300 is specified by a longitudinal range of interest 304 at least partially overlapping with an associated sample 306. The longitudinal range of interest 304 has a front boundary 308.

The optical means has at least two optical paths with an optical path length difference, and suitably provides two replicas of the optical radiation propagating therethrough. For illustration purposes the optical means is depicted in FIG. 3 as an optical fiber Michelson interferometer 310. A skilled artisan will appreciate that the optical means is capable of being implemented as any other interferometer known in the art, for example and without limitation, as a Mach-Zehnder interferometer. The Michelson interferometer 310 includes splitting and combining means 312 optically coupled with a first arm 314 and a second arm 316. The Michelson interferometer 310 includes also Faraday mirrors 318, 320 placed at the end of the first and second arms 314, 316, respectively. Those skilled in the art will recognize, that the splitting and combining means 312 is implemented, for example, and without limitation, as a 3 dB directional coupler. Those skilled in the art will also appreciate, that the embodiment as depicted in FIG. 3, is not limited to the use of a 3 dB directional coupler. Other splitting means employing a different splitting ratio may be suitably used without departing from the scope of the subject application.

The arms 314, 316 of the Michelson interferometer 310 have an initial optical path length difference for the two replicas of optical radiation propagating therethrough. As will be evident to a skilled artisan, the initial value of the optical path length difference is capable of being adjusted in the process of assembling the Michelson interferometer 310. Preferably, at least one arm of the Michelson interferometer 310 includes means adapted for changing the optical path length difference for the two replicas of optical radiation propagating therethrough. As will be recognized by those skilled in the art, the means adapted for changing the optical path length difference for the two replicas of optical radiation is capable of being implemented as any suitable means known in the art, such as for example, and without limitation, a suitable delay line or a phase modulator. Thus, in the embodiment of FIG. 3, the arms 314, 316 include piezoelectric optical fiber delay elements 326, 328, respectively. In the embodiment of FIG. 3, the splitting and combining means 312 of the Michelson interferometer 310 is coupled to a directional means 322 via an optical fiber 324.

The common path time domain optical coherence reflectometry/tomography device 300 further includes delivering means coupled with the directional means 322. In the embodiment of FIG. 3, the delivering means is optically coupled with the directional means 322 via an optical fiber 326. The embodiment of FIG. 3 illustrates the delivering means implemented as an optical fiber probe 328, which includes a proximal part 330 and a distal part 332. The distal part 332 of the optical fiber probe 328 includes a partially optically transparent non-specular reference reflector 334 placed at a predetermined optical path length from the front boundary 308 of the longitudinal range of interest 304. The optical fiber probe 328 includes an optical fiber 336. In the embodiment depicted in FIG. 3, the optical fiber probe 328 includes a sheath 338 and an output window 340. The output window 340 is placed in a vicinity of an associated sample 306.

In the embodiment of FIG. 3, the partially optically transparent non-specular reference reflector 334 is attached to an interior surface of the output window 340. The partially optically transparent non-specular reference reflector 334 is thus placed in a vicinity of an associated sample 306 at a predetermined optical path length from the front boundary of the longitudinal range of interest of an associated sample 306. The optical path length difference for the two replicas of the optical radiation propagating via the Michelson interferometer 310 is generally equal to the predetermined optical path length between the partially optically transparent non-specular reference reflector 334 and the front boundary 308 of the longitudinal range of interest 304. A skilled artisan will recognize that the optical fiber probe 328, the same as the optical fiber probe 106 in the embodiment of FIG. 1, also includes a focusing system (not shown) in its distal part 332. As will be appreciated by those skilled in the art, a tip 342 of the optical fiber 336 is capable of being moved to provide lateral scanning.

The optical fiber probe 328 provides forming and delivering of an optical radiation beam, including the first and second replicas, to the partially optically transparent non-specular reference reflector 334, and delivering a first portion of the optical radiation beam to an associated sample 308 (sample portion) via the partially optically transparent non-specular reference reflector 334, along a common optical path. In this embodiment, the partially optically transparent non-specular reference reflector 334 also provides splitting of the optical radiation beam, including the first and second replicas, into two portions, prior to delivery of the first portion of the optical radiation beam to an associated sample 308. The second portion is reflected by the partially optically transparent non-specular reference reflector 334 and serves as a non-specular reference reflection (reference portion). As will be recognized by a skilled artisan, the first portion of the optical radiation beam comprises a first portion of the first and second replicas, and the second portion of the optical radiation beam comprises a second portion of the first and second replicas.

The common path time domain optical coherence reflectometry/tomography device 300 further includes a time domain optoelectronic registering unit 344 optically coupled with the directional means 322. The time domain optoelectronic registering unit 344 includes a data processing and displaying unit (not shown in the drawing). A skilled artisan will appreciate that the time domain optoelectronic registering unit 344 is capable of being implemented as any suitable registering unit known in the art. A slow delay line suitably adapted to control the axial position of the observation zone is capable of being introduced in any of the arms of the Michelson interferometer 310 (not shown in the drawing). As will be appreciated by a skilled artisan, in the embodiment of FIG. 3, a suitable isolator or circulator may be required between the source 302 of optical radiation and the Michelson interferometer 310.

Figure 4:
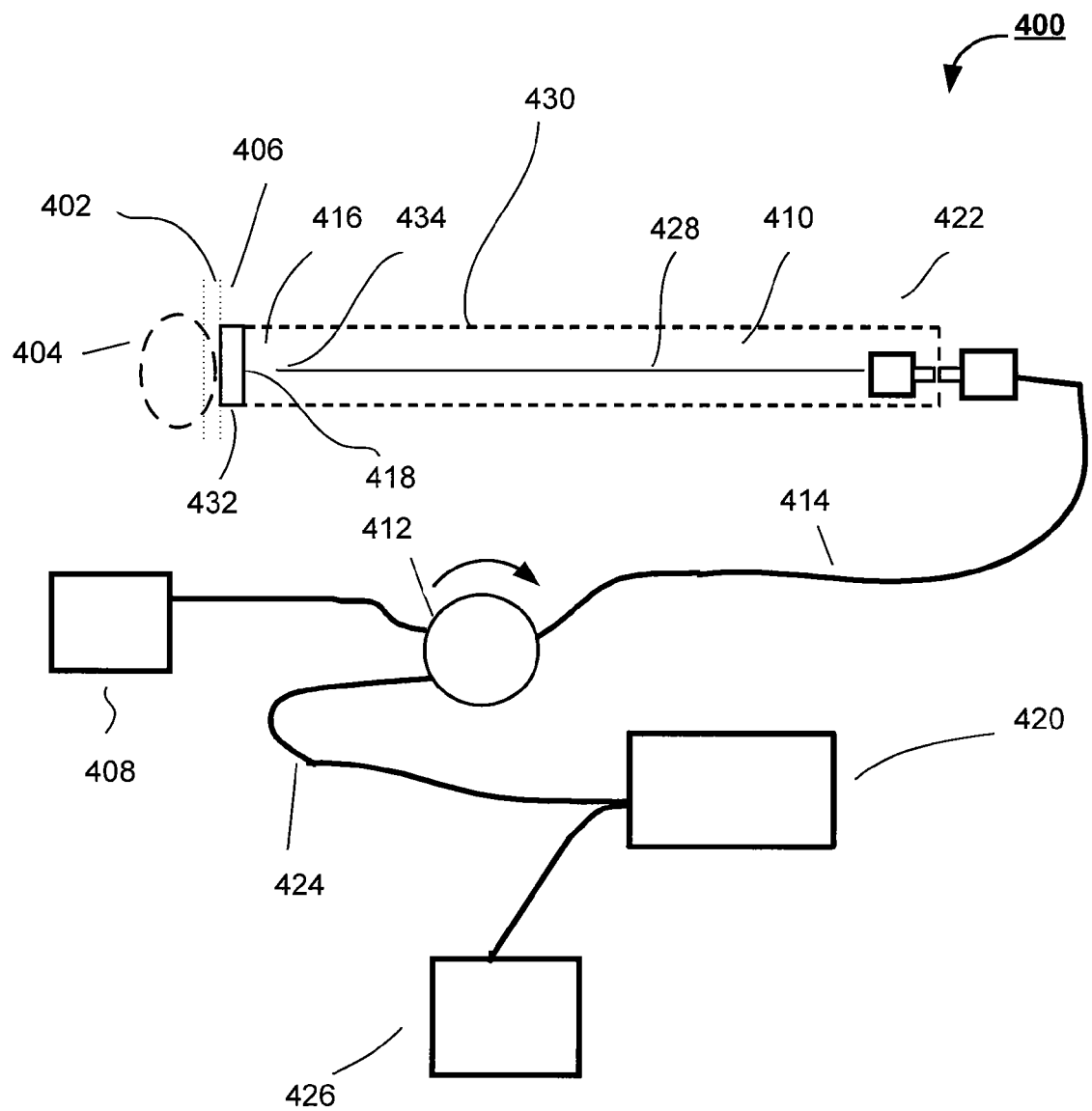
FIG. 4 is a schematic diagram of a common path time domain optical coherence tomography device according to another embodiment of the subject application.

Turning now to FIG. 4, there is shown a block diagram of a common path time domain reflectometry/tomography device 100 in accordance with another embodiment of the subject application. The common path time domain OCT device 400 is specified by a longitudinal range of interest 402 at least partially overlapping with an associated sample 404. The longitudinal range of interest 402 has at least a front boundary 406. The system includes a source 408 of optical radiation optically coupled with delivering means 410 via directional means 412 and an optical fiber 414. As will be appreciated by a skilled artisan, the source 408 of optical radiation is capable of being implemented analogous to the means adapted for producing an optical radiation described with respect to FIG. 3. A distal part 416 of the delivering device 410 includes a partially optically transparent non-specular reference reflector 418. In the embodiment of FIG. 4, the partially optically transparent non-specular reference reflector 418 is attached to an interior surface of the output window 432 and thus placed in a vicinity of an associated sample 404 at a predetermined optical path length from the front boundary 406 of the longitudinal range of interest 402. The delivering means 410 provides forming and delivering of an optical radiation beam to the partially optically transparent non-specular reference reflector 418, and delivering of a first portion of the optical radiation beam to an associated sample 404 (sample portion) via the partially optically transparent non-specular reference reflector 418, along a common optical path.

In this embodiment, the partially optically transparent non-specular reference reflector 418 provides splitting of the optical radiation delivered from the source 408 into two portions, prior to delivery of the first portion of the optical radiation beam to an associated sample 404. The second portion is reflected by the partially optically transparent non-specular reference reflector 418 and serves as a non-specular reference reflection (reference portion). The system 400 also includes optical means 420 that is in optical communication with a proximal part 422 of the delivering device 410 via an optical fiber 424, the directional means 412, and the optical fiber 414. The optical means 420 provides splitting of the sample portion and the non-specular reference portion into two replicas and further combining respective replicas to produce a combination optical radiation. A skilled artisan will appreciate that the optical means 420 is capable of being implemented as any optical interferometer known in the art, for example and without limitation, as a Michelson interferometer, a Mach-Zehnder interferometer, and the like. For example, and without limitation, the optical means 420 is capable of implementation analogous to the optical means 310 described above with reference to FIG. 3.

The two replicas are produced such that they have an optical path length difference. The optical means 420 includes means adapted for changing the optical path length difference for the two replicas of the optical radiation (not shown in the drawing). As will be recognized by a skilled artisan, the means adapted for changing the optical path length difference for the two replicas of optical radiation is capable of being implemented as any suitable means known in the art, such as for example, and without limitation, a suitable delay line or a phase modulator. The optical path length difference for the two replicas of optical radiation is generally equal to the predetermined optical path length between the partially optically transparent non-specular reference reflector 418 and the front boundary 406 of the longitudinal range of interest 402. The common path time domain optical coherence tomography device further includes a time domain optoelectronic registering unit 426 optically coupled with the optical means 420 and including a data processing and displaying unit (not shown).

In the embodiment of FIG. 4 the delivering means 410 is implemented as an optical fiber probe and thus includes an optical fiber 428. In the embodiment depicted in FIG. 4, the delivering means 410 includes a sheath 430 and an output window 432. The output window 432 is placed in a vicinity of an associated sample 404. In the embodiment of FIG. 4 the partially optically transparent non-specular reference reflector 418 is attached to an interior surface of the output window 432. The tip 434 of the optical fiber 428 is capable of being moved to provide lateral scanning in the manner discussed above.

Those skilled in the art will recognize that the partially optically transparent non-specular reference reflector 214 is described in detail with respect to the embodiment illustrated in FIG. 2. However, this description applies, as well, to the partially optically transparent non-specular reference reflector 118, 340, and 418 of the embodiments in FIG. 1, FIG. 3, and FIG. 4, respectively.

As will be further appreciated by those skilled in the art, the systems 100, 300, and 400 are also capable of including means adapted for changing relative positions of an associated sample 108, 306, and 404 and the optical radiation beam being delivered to an associated sample 108, 306, and 404 (the means not shown in respective drawings). A skilled artisan will also appreciate that the means adapted for changing relative positions of an associated sample 108, 306, and 404 and the optical radiation beam being delivered to an associated sample 108, 306, and 404 suitably provides lateral scanning of the optical radiation beam. Those skilled in the art will recognize that the means providing lateral scanning is suitably capable of being implemented in any way known in the art, for example and without limitation, as a lateral scanner incorporated into the delivering means, or as an element for changing the position of the associated sample, as known in the art. Modifications of the common path frequency domain and time domain optical coherence tomography and reflectometry devices and of the delivering device for optical radiation are illustrated herein by means of examples of optical fiber devices although it is evident that they may be implemented with the use of bulk optic elements. The optical fiber implementation is preferable for use in medical applications, especially in endoscopy, where flexibility of the optical fiber provides convenient access to different tissues and organs, including internal organs via an endoscope. However, as a skilled artisan will understand, the devices in whole, or any part of them, can be implemented using traditional bulk optics: mirrors, prisms etc.

The operation of the common path frequency domain optical coherence reflectometry/tomography device 100 and of the delivering device 200 in accordance with the subject application will be best understood from the following description of carrying out the method for common path frequency domain optical measurements in accordance with the subject application.

Referring now to FIG. 1, the method begins with providing an optical radiation, for example and without limitation, in the visible or near IR range from the source 102. The optical radiation is directed by the directional means 104 to the optical fiber probe 106 via the optical fiber 110. The optical fiber probe 106, a schematic diagram of which is shown in FIG. 2 as the optical fiber probe 200, is placed such that the exterior surface of the output window 114 (output window 210 in FIG. 2) is in a vicinity of an associated sample 108 (associated sample 212 in FIG. 2). The optical fiber probe 106 forms an optical radiation beam from the optical radiation directed to the proximal part 112 of the optical fiber probe 106. The optical radiation beam and a first portion of the optical radiation beam are delivered, correspondingly, to the partially optically transparent non-specular reference reflector 118, which in FIG. 2 is designated as the reference reflector 214, and to an associated sample 108, designated in FIG. 2 as an associated sample 212, via the partially optically transparent non-specular reference reflector 118, along a common optical path.

Prior to delivery of the first portion of the optical radiation beam to an associated sample 108, the partially optically transparent non-specular reference reflector 118 splits the optical radiation beam into a first and second portions. The second portion is reflected by the partially optically transparent non-specular reference reflector 118. The partially optically transparent non-specular reference reflector 118 then creates a combination optical radiation by combining an optical radiation returning from an associated sample 108 with a non-specular reference optical radiation reflected from the partially optically transparent non-specular reference reflector 118. Lateral scanning of the optical radiation beam is provided by the means adapted for changing relative positions of an associated sample 108 and the optical radiation beam being delivered to an associated sample 108 in the manner discussed above. As will be recognized by those skilled in the art, the combining is performed analogous to that in a frequency domain OCT device known in the art using a specular reference reflection. However, as will be further appreciated by a skilled artisan, since the optical path length shift between the sample and reference portions of optical radiation is significantly decreased in comparison with a typical frequency domain OCT device known in the art, high frequency fringes are substantially reduced. In addition, the reference reflection from the partially optically transparent reference reflector 118 has a stable power level over the lateral scanning range.

The combination optical radiation is then delivered by the optical fiber probe 106 to the directional means 104 via the optical fiber 110. The directional means 104 further directs the combination optical radiation to the frequency domain optoelectronic registering means 124. The frequency domain optoelectronic registering means 124 performs frequency domain optoelectronic registration of the combination optical radiation, the latter being representative of the optical radiation returning from an associated sample 108. The optical spectrum of the combination optical radiation registered by the frequency domain optoelectronic registering means 124, has all necessary information about the in-depth coherent reflection profile by including a component that is Fourier conjugate of the in-depth profile of an associated sample 108. Thus, the profile is extracted from Fourier transformation of the optical spectrum of the combined optical radiation by the data processing and displaying unit of the frequency domain optoelectronic registering unit 132.

The operation of the common path time domain optical coherence reflectometry/tomography device 300 in accordance with the subject application will be best understood from the following description of carrying out the method for common path time domain optical measurements in accordance with the subject application.

Referring now to FIG. 3, the method begins with providing an optical radiation, for example and without limitation, in the visible or near IR range from the source 302. The optical radiation from the source 302 is split by the Michelson interferometer 310 into a first and second replicas of the optical radiation, propagating therethrough with an optical path length difference. As mentioned above, the optical path length difference between the first and second replicas of optical radiation is generally equal to the predetermined optical path length between the partially optically transparent non-specular reference reflector 334 and the front boundary 308 of the longitudinal range of interest 304. With respect to FIG. 3 with the Michelson interferometer 310 used as the optical means, the splitting and combining means 312 directs the first replica of the optical radiation incoming from the source 302 along the first arm 314 and directs the second replica of the optical radiation incoming from the source 302 along the second arm 316 of the Michelson interferometer 310. The two replicas of optical radiation after being reflected from respective Faraday mirrors 318, 320 enter the splitting and combining means 312. The splitting and combining means 312 directs the two replicas of optical radiation to the directional element 322 via the optical fiber 324. Next, the two replicas of optical radiation, being shifted due the optical path length difference between the first arm 314 and the second arm 316 of the interferometer 310, are directed to the proximal part 330 of the optical fiber probe 328 via the optical fiber 326. As will be recognized by those skilled in the art, the optical fiber probe 328 is placed such that the exterior surface of the output window 340 is in a vicinity of an associated sample 306.

The optical fiber probe 328 forms an optical radiation beam including the first and second replicas from the optical radiation incoming the proximal part 330 of the optical fiber probe 328. The optical radiation beam and a first portion of the optical radiation beam are delivered, correspondingly, to the partially optically transparent non-specular reference reflector 334 and to an associated sample 306, via the partially optically transparent non-specular reference reflector 334, along a common optical path. Prior to delivery of the first portion of the optical radiation beam to an associated sample 306, the partially optically transparent non-specular reference reflector 334 splits the optical radiation beam including the first and second replicas, into a first and second portions. The second portion of the optical radiation beam including the first and second replicas is reflected by the partially optically transparent non-specular reference reflector 334.

The partially optically transparent non-specular reference reflector 334 then creates a combination optical radiation by combining an optical radiation representative of one replica, returning from an associated sample 306, with a non-specular reference optical radiation, representative of the other replica, reflected from the partially optically transparent non-specular reference reflector 334. Lateral scanning of the optical radiation beam is provided by the means adapted for changing relative positions of an associated sample 306 and the optical radiation beam being delivered to an associated sample 306, in the manner discussed above. As will be recognized by those skilled in the art, the combining is suitably performed analogous to that in a respective time domain OCT device known in the art, using a specular reference reflection. However, as will be further appreciated by a skilled artisan, the reference reflection being non-specular has a stable power level over the lateral scanning range. The combination optical radiation is then delivered by the optical fiber probe 328 to the directional means 322 via the optical fiber 326. The directional means 322 further directs the combination optical radiation to the time domain optoelectronic registering means 344. The time domain optoelectronic registering means 344 performs time domain optoelectronic registration of the combination optical radiation, the latter being representative of the optical radiation returning from an associated sample 306.

Referring now to FIG. 4, the method begins with providing an optical radiation, for example and without limitation, in the visible or near IR range from the source 408. The optical radiation from the source 408 is directed by the directional means 412 to the delivering means 410 via the optical fiber 414. The delivering means 410 is placed such that the exterior surface of the output window 432 is in a vicinity of an associated sample 404. The delivering means 410 forms an optical radiation beam from the incoming optical radiation. The optical radiation beam and a first portion of the optical radiation beam are delivered, correspondingly, to the partially optically transparent non-specular reference reflector 418 and to an associated sample 404 via the partially optically transparent non-specular reference reflector 418, along a common optical path.

Prior to delivery of the first portion of the optical radiation beam to an associated sample 404, the partially optically transparent non-specular reference reflector 418 splits the optical radiation beam into a first and second portions. The second portion is reflected by the partially optically transparent non-specular reference reflector 418. The optical radiation returning from an associated sample 404 and an optical radiation reflected from the partially optically transparent non-specular reference reflector 418 is then delivered to the optical means 420 via the optical fiber 414 and the directional means 412. The optical means 420 splits the optical radiation returning from an associated sample 404 into a first and second replicas propagating therethrough with an optical path length difference, which is generally equal to the predetermined optical path length between the partially optically transparent non-specular reference reflector 418 and the front boundary of the longitudinal range of interest 402. The optical means 420 further splits the optical radiation reflected from the partially optically transparent non-specular reference reflector 418 into a first and second non-specular reference replicas propagating therethrough with an optical path length difference, which is generally equal to the optical path length difference for the first and second replicas of the optical radiation returning from an associated sample 404. The optical means 420 then creates a combination optical radiation by combining a replica of the optical radiation returning from an associated sample 404 with a respective non-specular reference replica of the non-specular optical radiation reflected from the partially optically transparent non-specular reference reflector 418. Lateral scanning of the optical radiation beam is provided by the means adapted for changing relative positions of an associated sample 404 and the optical radiation beam being delivered to an associated sample 404 in the manner discussed above. As will be recognized by those skilled in the art, the combining is suitably performed analogous to that in a respective time domain OCT device known in the art, using a specular reference reflection and a secondary interferometer. However, as will be further appreciated by a skilled artisan, the reference reflection from the partially optically transparent non-specular reference reflector 418 has a stable power level over the lateral scanning range. The combination optical radiation is then directed to the time domain optoelectronic registering means 426. Lateral scanning of the optical radiation beam is also provided by the means adapted for changing relative positions of an associated sample 404 and the optical radiation beam being delivered to an associated sample 404, as discussed in detail above. The time domain optoelectronic registering means 426 performs time domain optoelectronic registration of the combination optical radiation, the latter being representative of the optical radiation returning from an associated sample 404.

Figure 5A:
FIG. 5 is an illustration of producing a combination optical radiation according to one embodiment of the subject application.
Figure 5B:
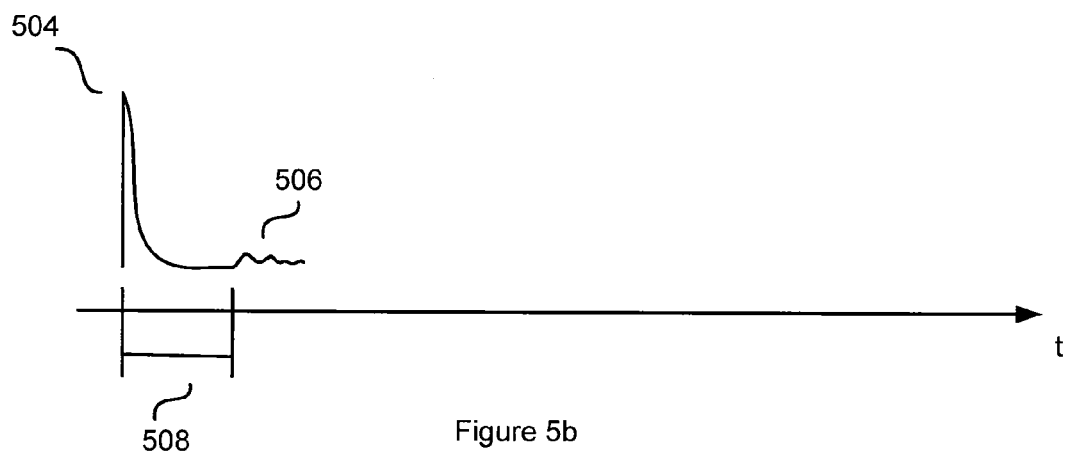
Figure 5C:
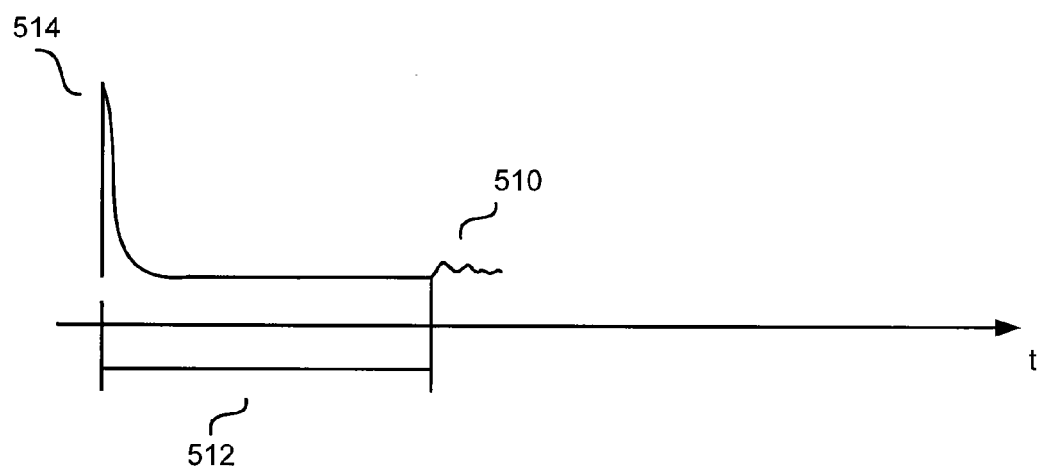

Turning now to FIG. 5, there is shown an illustration 500 of producing a combination optical radiation in accordance with the present invention with reference to the embodiment depicted in FIG. 1. For illustration purposes the optical radiation is represented by an imaginary short pulse propagating therethrough and placed along a time axis t in FIG. 5. Thus, FIG. 5a illustrates the optical radiation entering the optical fiber probe 106 via the directional element 104 of FIG. 1. FIG. 5b illustrates the optical radiation after it has been split into two portions (a reference portion 504 and a sample portion 506) by the partially optically transparent non-specular reference reflector 118 of the optical fiber probe 106. As shown in FIG. 5b, the sample portion 506 has a time shift 508, and hence, a respective optical path length shift with respect to the reference portion 504. The sample portion 506 of the optical radiation is combined with the reference portion 504 reflected from the partially optically transparent non-specular reference reflector 118, the combining being performed by the partially optically transparent non-specular reference reflector 118. FIG. 5c illustrates splitting of the optical radiation by a specular reference reflector in a known embodiment of an optical fiber probe with, for example, the tip of the optical fiber probe serving as a reference reflector. As depicted in FIG. 5c, the sample portion 510 has a time shift, and hence, a respective optical path length shift 512 with respect to the reference portion 514. As will be appreciated by those skilled in the art, the optical path length shift between the sample and reference portions of optical radiation in the embodiment of the subject application is significantly decreased in comparison with a typical frequency domain OCT device known in the art. As will be further recognized by a skilled artisan, the latter substantially reduces high frequency fringes in the combination optical radiation.

Figure 6A:
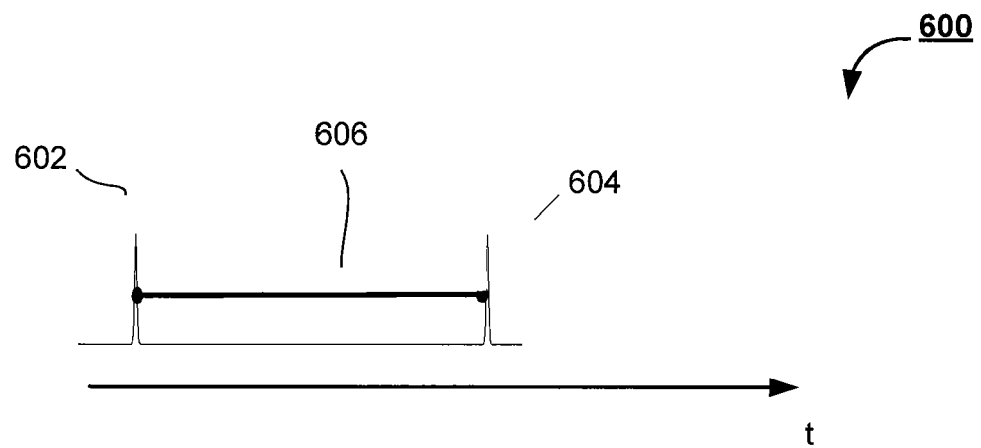
FIG. 6 is an illustration of producing a combination optical radiation according to another embodiment of the subject application.
Figure 6B:
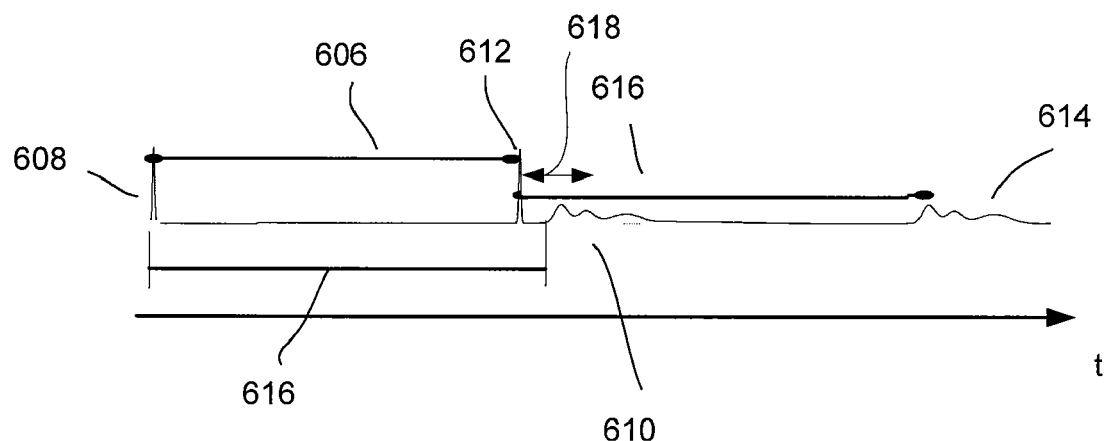

Turning now to FIG. 6, there is shown an illustration 600 of producing a combination optical radiation in accordance with the present invention with reference to the embodiment depicted in FIG. 3. For illustration purposes the optical radiation is represented by an imaginary short pulse propagating therethrough and placed along a time axis t in FIG. 6. Thus, FIG. 6a illustrates the optical radiation entering the optical fiber probe 328 via the directional element 322 of FIG. 3, after the optical radiation from the source 302 is divided into two replicas shifted along the time axis by the Michelson interferometer 310. The two replicas are illustrated in FIG. 6a as respective short pulses 602 and 604. As will be recognized by a skilled artisan, the time shift 606 between the two replicas 602 and 604 of the optical radiation is defined by the optical path length difference between the arms 314, 316 of the Michelson interferometer 310. FIG. 6b illustrates the two replicas after each of them were split into two portions (a reference portion and a sample portion) by the partially optically transparent non-specular reference reflector 334 of the optical fiber probe 328. As shown in FIG. 6b, the reference portion 608 of the first replica has a shift 616 with respect to the sample portion 610 of the same replica. Also, the reference portion 612 of the second replica has a shift 516 with respect to the sample portion 614 of the same replica. Those skilled in the art will appreciate that the reference portion of one replica interferes with the sample portion of the other replica in the same manner as in a previously known common path time domain optical coherence reflectometry device with a secondary interferometer. Arrows 618 illustrate changing the optical path length difference for the two replicas of optical radiation propagating via the Michelson interferometer 310 for obtaining an in-depth profile of an associated sample 306 in the manner known in the art.

As will be recognized by those skilled in the art, the above illustration may be suitably applied to the OCT device illustrated in FIG. 4 keeping in mind that the combining is performed in the optical means 420.

The foregoing description of preferred embodiments of the subject application has been presented for purposes of illustration and description. It is not intended to be exhaustive or to limit the subject application to the precise form disclosed. Obvious modifications or variations are possible in light of the above teachings. The embodiment was chosen and described to provide the best illustration of the principles of the subject application and its practical application to thereby enable one of ordinary skill in the art to use the subject application in various embodiments and with various modifications as are suited to the particular use contemplated. All such modifications and variations are within the scope of the subject application as determined by the appended claims when interpreted in accordance with the breadth to which they are fairly, legally and equitably entitled.

What is claimed:

1. A common path frequency domain optical coherence reflectometry device comprising:
    means adapted for generating an optical radiation;
    delivering means comprising:
        a proximal part, and
        a distal part including a focusing system and a partially optically transparent non-specular reference reflector, which is optically coupled with the focusing system, wherein the delivering means is adapted for forming and delivering an optical radiation beam to the partially optically transparent non-specular reference reflector, and delivering a first portion of the optical radiation beam to an associated sample via the partially optically transparent non-specular reference reflector placed in a vicinity of an associated sample, along a common optical path;
    directional means optically coupled with the means adapted for generating optical radiation and adapted for directing the optical radiation from the means adapted for generating optical radiation to the proximal part of the delivering means; and
    frequency domain optoelectronic registering means optically coupled with the directional means and comprising data processing and displaying means;
    wherein the partially optically transparent non-specular reference reflector is adapted for splitting the optical radiation beam into two portions prior to delivery of the first portion of the optical radiation beam to an associated sample, wherein the second portion is reflected by the partially optically transparent non-specular reference reflector;
    wherein the partially optically transparent non-specular reference reflector is further adapted for creating a combination optical radiation by combining an optical radiation returning from an associated sample with a non-specular reference optical radiation reflected from the partially optically transparent non-specular reference reflector;
    wherein the delivering means is further adapted for delivering the combination optical radiation to the directional means; and
    wherein the directional means is further adapted for directing the combination optical radiation to the frequency domain optoelectronic registering means.

2. The common path frequency domain optical coherence reflectometry device of claim 1, wherein the delivering means is an optical fiber probe comprising:
an output window at its distal end placed in a vicinity of an associated sample; and
an optical fiber extending therethrough and optically coupled with the focusing system and with the partially optically transparent non-specular reference reflector;
wherein the partially optically transparent non-specular reference reflector is an integral part of the output window.

3. The common path frequency domain optical coherence reflectometry device of claim 1 wherein the means adapted for generating an optical radiation is a tunable source of optical radiation, and wherein the frequency domain optoelectronic registering means includes at least one photodetector connected with the data processing and displaying means.

4. The common path frequency domain optical coherence reflectometry device of claim 1 wherein the means adapted for generating an optical radiation is a source of low-coherence optical radiation, and wherein the frequency domain optoelectronic registering means includes a spectrometer connected with the data processing and displaying means.

5. The common path frequency domain optical coherence reflectometry device of claim 1 further including means adapted for changing relative positions of an associated sample and the optical radiation beam being delivered to an associated sample, and wherein the common path frequency domain optical coherence reflectometry device is part of a common path frequency domain optical coherence tomography device.

6. A method for common path frequency domain optical measurements, comprising the steps of:
generating an optical radiation;
forming an optical radiation beam;
delivering the optical radiation beam to a partially optically transparent non-specular reference reflector and delivering a first portion of the optical radiation beam to an associated sample via the partially optically transparent non-specular reference reflector placed in a vicinity of an associated sample, along a common optical path;
splitting the optical radiation beam into a first and second portions prior to delivery of the first portion of the optical radiation beam to an associated sample, the second portion being reflected by the partially optically transparent non-specular reference reflector, wherein the step of splitting is performed by the partially optically transparent non-specular reference reflector;
creating a combination optical radiation by combining an optical radiation returning from an associated sample within the predetermined angle of view, with a non-specular reference optical radiation reflected from the partially optically transparent non-specular reference reflector, the step of combining being performed by the partially optically transparent non-specular reference reflector; and
performing frequency domain optoelectronic registration of the combination optical radiation, the latter being representative of the optical radiation returning from an associated sample.

7. The method for common path frequency domain optical measurements of claim 6 further comprising the step of changing relative positions of an associated sample and an optical radiation beam being delivered to an associated sample, providing thereby common path frequency domain optical coherence tomography imaging of an associated sample.

* * * * *